(12) United States Patent
Billich et al.

(10) Patent No.: US 7,378,416 B2
(45) Date of Patent: May 27, 2008

(54) MIF-INHIBITORS

(76) Inventors: Andreas Billich, Dr. Gohrengasse 25, Mödling (AT) 2340; Philipp Lehr, Technikerstrasse 30/18, Mödling (AT) 2340; Hubert Gstach, Breite Gasse 17/5, Vienna (AT) 1070

( * ) Notice: Subject to any disclaimer, the term of this patent is extended or adjusted under 35 U.S.C. 154(b) by 0 days.

(21) Appl. No.: 11/576,610

(22) PCT Filed: Oct. 19, 2005

(86) PCT No.: PCT/EP2005/011233

§ 371 (c)(1),
(2), (4) Date: Apr. 24, 2007

(87) PCT Pub. No.: WO2006/045505

PCT Pub. Date: May 4, 2006

(65) Prior Publication Data

US 2007/0219189 A1    Sep. 20, 2007

(30) Foreign Application Priority Data

Oct. 21, 2004 (GB) .................. 0423405.0

(51) Int. Cl.
*A61K 31/535* (2006.01)
*A61P 29/00* (2006.01)
*C07D 265/18* (2006.01)
*C07D 413/04* (2006.01)

(52) U.S. Cl. ..................... 514/230.5; 544/90

(58) Field of Classification Search .............. 544/50, 544/90; 514/224.2, 230.5
See application file for complete search history.

(56) References Cited

OTHER PUBLICATIONS

C. Cimarelli: "A facile synthesis of 3,4-dialkyl-3, 4-2H-1, 3-benzoxazin-2-ones and naphthoxazin-2ones and their reactions with organolithium and grignard reagents—prepraration of N-'1-(2'-hydroxyphenyl) alkyl amides", Canadian Journal of Chemistry, vol. 82, No. 8, pp. 1314-1321, (2004).

O. Masaya et al., "Coumarain and chromen-4-one analogues as tautomerase inhibitors of macrophage migration inhibitors of macrophage migration inhibitory factor: discovery and x-ray crystallography", Journal Med. Chem, vol. 44, pp. 540-547, (2001).

*Primary Examiner*—Kahsay T Habte
(74) *Attorney, Agent, or Firm*—Novartis; John B. Alexander

(57) ABSTRACT

3,4-dihydro-benzo[e][1,3]oxazin-2-ones which are substituted at the nitrogen atom by unsubstituted or substituted $(C_{3-8})$cycloalkyl, $(C_{1-4})$alkyl$(C_{3-8})$cycloalkyl, $(C_{6-18})$aryl or $(C_{6-18})$aryl$(C_{1-4})$alkyl and their use as pharmaceuticals.

10 Claims, No Drawings

MIF-INHIBITORS

The present invention relates to MIF-inhibitors, such as compounds which are pharmaceutically active, e.g. inhibitors of the tautomerase activity of the human macrophage migration inhibitory factor (MIF), such as 3,4-dihydro-benzo[e][1,3]oxazin-2-ones which are substituted at the nitrogen atom by unsubstituted or substituted $(C_{3-8})$cycloalkyl, $(C_{3-8})$cycloalkyl$(C_{1-4})$alkyl, $(C_{6-18})$aryl, or $(C_{6-18})$aryl$(C_{1-4})$alkyl.

MIF is a cytokine with a wide variety of cellular and biological activities (for reviews see: Calandra et al., Nat. Rev. Immunol. 3:791-800. 2003; Orita et al., Curr. Pharm. Design 8:1297-1317, 2002; Nishihira, J Interferon Cytokine Res 20:751-762, 2000; Swope & Lolis, Rev. Physiol. Biochem. Pharmacol. 139:1-32, 1999; Metz & Bucala, Adv. Immunol. 66:197-223, 1997). MIF was found to inhibit the random migration of macrophages, and to be associated with delayed-type hypersensitivity reactions (George & Vaughan, Proc. Soc. Exp. Biol. Med. 111:514-521, 1962; Weiser et al., J. Immunol. 126:1958-1962, 1981; Bloom & Bennett, Science, 153:80-82, 1966; David, Proc. Natl. Acad. Sci. USA 56:72-77, 1966). MIF was also shown to enhance macrophage adherence, phagocytosis and tumoricidal activity (Nathan et al., J. Exp. Med. 137:275-288, 1973; Nathan et al., J. Exp. Med. 133:1356-1376, 1971; Churchill et al., J. Immunol. 115:781-785, 1975).

Recombinant human MIF was originally cloned from a human T cell library (Weiser et al., Proc. Natl. Acad. Sci. USA 86: 7522-7526, 1989), and was shown to activate blood-derived macrophages to kill intracellular parasites and tumor cells in vitro, to stimulate IL-1β and TNFα expression, and to induce nitric oxide synthesis (Weiser et al., J. Immunol. 147:2006-2011, 1991; Pozzi et al., Cellular Immunol. 145:372-379, 1992; Weiser et al., Proc. Natl. Acad. Sci. USA 89:8049-8052, 1992; Cunha et al., J. Immunol. 150:1908-1912, 1993).

More recently it has been found that MIF is not only a cytokine product of the immune system, but also is a hormone-like product of the endocrine system, particularly the pituitary gland. This work has underscored the potent activity of MIF as a counter-regulator of the anti-inflammatory effects of the glucocorticoids (both those endogenously released and those therapeutically administered), with the effect that the normal activities of glucocorticoids to limit and suppress the severity of inflammatory responses are inhibited by MIF and the endogenous MIF response may thus seen as a cause or an exacerbative factor in a variety of inflammatory diseases and conditions (reviewed in Donnelly and Bucala, Molecular Medicine Today 3:502-507, 1997).

Additional biological activities include the regulation of stimulated T cells (Bacher et al., Proc. Natl. Acad. Sci. USA 93:7849-7854, 1996), the control of IgE synthesis (Mikayama et al., Proc. Natl. Acad. Sci. USA 90:10056-60, 1993), the functional inactivation of the p53 tumor suppressor protein (Hudson et al., J. Exp. Med. 190:1375-1382, 1999), the regulation of glucose and carbohydrate metabolism (Sakaue et al., Mol. Med. 5:361-371, 1999), and the regulation of tumor cell growth and of angiogenesis (Chesney et al., Mol Med. 5:181-191, 1999; Shimizu et al., Biochem. Biophys. Res. Commun. 264:751-758, 1999; Mitchell & Bucala, Cancer Biol. 10:359-366, 2000). A role of MIF in atherogenesis (Lin et al., Circulation Res. 8:1202-1208, 2000), in asthma (Yamaguchi et al., Clin. Exp. Allergy 30:1244-1249, 2000), and in malaria (Martiney et al., Infection Immunity 68:2259-2267, 2000) has also been implicated.

Anti-MIF antibodies have been shown to be active in a variety of models: endotoxin- and exotoxin-induced toxic shock (Bernhagen et al., Nature, 365:756-759, 1993; Kobayashi et al., Hepatology, 29:1752-1759, 1999; Calandra et al., Proc. Natl. Acad. Sci. USA., 95:11383-11388, 1998; Makita et al., Am. J. Respir. Crit. Care Med. 158:573-579, 1998, Calandra et al., Nat. Med. 6:164-170, 2000), T-cell activation (Bacher et al., Proc. Natl. Acad. Sci. USA. 93:7849-7854, 1996), autoimmune diseases, including rheumatoid arthritis (Leech et al., Arthritis Rheum., 42:1601-1608, 1999), uveoretinitis (Kitaichi et al., Curr. Eye Res., 20:109-114, 2000), glomerulonephritis (Yang et al., Mol. Med. 4: 413-424, 1998), experimental acute encephalomyelitis (Denkinger et al., J. Immunol. 170: 1274-1282, 2003) colitis (de Jong et al., Nat. Immunol. 2:1061-1066, 2001; Ohkawara et al., Gastroenterol. 123: 256-270, 2002), and skin graft destruction (Hou et al., Transplantation 72: 1890-1897, 2001), and atherosclerosis (Chen et al. Arterioscler. Thromb. Vasc. Biol. 24:709-714, 2004; Schober et al., Circulation 109:380-385, 2004). Furthermore, anti-MIF antibodies have been shown to inhibit tumor growth and angiogenesis (Chesney et al., Mol. Med. 5:181-191, 1999; Ogawa et al., Cytokine 12:309-314, 2000; Mitchell & Bucala, Cancer Biol. 10:359-366, 2000). Based on the activity of the anti-MIF antibodies, the therapeutic potential of low molecular weight MIF-inhibitors is high.

MIF shares significant sequence homology (36% identity) with D-dopachrome tautomerase, and has enzymatic activity to catalyze the tautomerization of the non-physiological substrates D-dopachrome (Rosengren et al., Mol. Med. 2:143-149, 1996) and L-dopachrome methyl ester (Bendrat et al., Biochemistry, 36:15356-15362, 1997) (FIG. 1A). Additionally, phenylpyruvic acid and p-hydroxyphenylpyruvic acid (Rosengren et al., FEBS Letter, 417:85-88, 1997), and 3,4-dihydroxyphenylaminechrome and norepinephrinechrome (Matsunaga et. al., J. Biol. Chem., 274:3268-3271, 1999) are MIF substrates. The three-dimensional crystal structure of human MIF reveals that the protein exists as a homotrimer (Lolis et al., Proc. Ass. Am. Phys. 108: 415-419, 1996). Various inhibitors of the MIF tautomerase activity have been described (e.g., Orita et al. J. Med. Chem. 44:540-547, 2001; Senter et al., Proc. Natl. Acad. Sci (USA) 99:144-149, 2002; Dios et al., J. Med. Chem. 45: 2410-2416, 2002; Lubetsky et al. J. Biol. Chem. 277:24976-24982, 2002).

We have now surprisingly found a novel class of compounds which acts as MIF-inhibitors.

In one aspect the present invention provides compounds selected from the group consisting of
3-(($C_{6-12}$)aryl)-3,4-dihydro-benzo[e][1,3]oxazin-2-ones,
 e.g. 3-(phenyl)-3,4-dihydro-benzo[e][1,3]oxazin-2-ones,
  3-(naphthyl)-3,4-dihydro-benzo[e][1,3]oxazin-2-ones,
3-(($C_{3-8}$)cycloalkyl)-3,4-dihydro-benzo[e][1,3]oxazin-2-ones,
 e.g. 3-(cyclohexyl)-3,4-dihydro-benzo[e][1,3]oxazin-2-ones,
3-(($C_{6-12}$)aryl($C_{1-4}$)alkyl)-3,4-dihydro-benzo[e][1,3]oxazin-2-ones,
 e.g. 3-(benzyl-3,4-dihydro-benzo[e][1,3]oxazin-2-ones, and
3-(($C_{3-8}$)cycloalkyl($C_{1-4}$)alkyl)-3,4-dihydro-benzo[e][1,3]oxazin-2-ones,
preferably
3-(phenyl)-3,4-dihydro-benzo[e][1,3]oxazin-2-ones,
3-(naphthyl)-3,4-dihydro-benzo[e][1,3]oxazin-2-ones,
3-(cyclohexyl)-3,4-dihydro-benzo[e][1,3]oxazin-2-ones, and 3-(benzyl)-3,4-dihydro-benzo[e][1,3]oxazin-2-ones,
3-(phenyl)-7-hydroxy-3,4-dihydro-benzo[e][1,3]oxazin-2-ones,
3-(naphthyl)-7-hydroxy-3,4-dihydro-benzo[e][1,3]oxazin-2-ones,
3-(cyclohexyl)-7-hydroxy-3,4-dihydro-benzo[e][1,3]oxazin-2-ones, and
3-(benzyl)-7-hydroxy-3,4-dihydro-benzo[e][1,3]oxazin-2-ones,
3-(phenyl)-7-aminosulfonyloxy-3,4-dihydro-benzo[e][1,3]oxazin-2-ones,
3-(naphthyl)-7-aminosulfonyloxy-3,4-dihydro-benzo[e][1,3]oxazin-2-ones,
3-(cyclohexyl)-7-aminosulfonyloxy-3,4-dihydro-benzo[e][1,3]oxazin-2-ones, and
3-(benzy)-7-aminosulfonyloxy-3,4-dihydro-benzo[e][1,3]oxazin-2-ones.

In another aspect the present invention provides a compound of formula

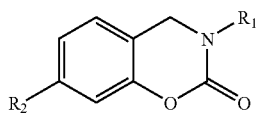

I e.g. which is a 3,4-dihydro-benzo[e][1,3]oxazin-2-one, wherein
$R_1$ is unsubstituted or substituted
$(C_{3-8})$cycloalkyl$(C_{1-4})$alkyl,
$(C_{6-18})$aryl$(C_{1-4})$alkyl,
$(C_{3-8})$cycloalkyl,
$(C_{6-18})$aryl,
e.g. wherein $(C_{6-18})$aryl is optionally annelated with another ring (system),
e.g. wherein substituents include, e.g. are selected from the group consisting of, $(C_{6-18})$aryl, halogen, hydroxy, aminosulfonyloxy, $(C_{1-4})$alkoxy, tri$(C_{1-6})$alkylsilyloxy, halo$(C_{1-4})$alkyl or halo$(C_{1-4})$alkoxy,
$R_2$ is hydrogen or unsubstituted or substituted hydroxy,
e.g. hydrogen, hydroxy, aminosulfonyloxy, $(C_{1-4})$alkoxy, tri$(C_{1-6})$alkylsilyloxy or halo$(C_{1-4})$alkoxy.

In a compound of formula I preferably
$R_1$ is unsubstituted or substituted
cyclohexyl,
phenyl, naphthyl,
phenyl annelated with another ring (system), e.g. annelated with a crown ether,
phenyl$(C_{1-4})$alkyl,
wherein substituents include, e.g. are selected from the group consisting of, $(C_{6-18})$aryl, halogen, hydroxy, aminosulfonyloxy, $(C_{1-4})$alkoxy, tri$(C_{1-6})$alkylsilyloxy, halo$(C_{1-4})$alkyl, halo$(C_{1-4})$alkoxy,
$R_2$ is hydrogen, hydroxy, aminosulfonyloxy, $(C_{1-4})$alkoxy, tri$(C_{1-6})$alkylsilyloxy, halo$(C_{1-4})$alkyl, or halo$(C_{1-4})$alkoxy.

In another aspect the present invention provides a compound of formula I, wherein $R_1$ is
cyclohexyl,
hydroxycyclohexyl, e.g. 4-hydroxycyclohexyl,
phenyl,
biphenylyl, e.g. biphenyl-4-yl,
napththyl, e.g. naphth-1-yl,
hydroxyphenyl, e.g. 3-hydroxyphenyl, 4-hydroxyphenyl,
methoxyphenyl, e.g. 4-methoxyphenyl,
trifloromethoxyphenyl, e.g. 4-trifloromethoxyphenyl,
bromophenyl, e.g. 4-bromophenyl,
aminosulfonyloxyphenyl, e.g. 3-aminosulfonyloxyphenyl, 4-aminosulfonyloxyphenyl,
(tert-butyl)(dimethyl)silyloxyphenyl, e.g. 4-(tert-butyl)(dimethyl)silyloxyphenyl,
phenylmethyl, or
phenyl annelated with a 18-crown-6, such as benzo-18-crown-6,
and $R_2$ is as defined above.

In another aspect the present invention provides a compound of formula I, wherein $R_1$ is as defined above, and $R_2$ is
hydrogen,
hydroxy,
aminosulfonyloxy.

In a compound of formula I each single defined substituent may be a preferred substituent, e.g. independently of each other substituent defined.

In another aspect the present invention provides a compound selected from the group consisting of
3-Cyclohexyl-7-hydroxy-3,4-dihydro-benzo[e][1,3]oxazin-2-one,
3-(4-Methoxyphenyl)-7-hydroxy-3,4-dihydro-benzo[e][1,3]oxazin-2-one,
3-(4-Hydroxycyclohexyl-7-hydroxy-3,4-dihydro-benzo[e][1,3]oxazin-2-one,
3-Phenyl-7-hydroxy-3,4-dihydro-benzo[e][1,3]oxazin-2-one,
3-(3-Hydroxyphenyl)-7-hydroxy-3,4-dihydro-benzo[e][1,3]oxazin-2-one,
3-(4-Hydroxyphenyl)-7-hydroxy-3,4-dihydro-benzo[e][1,3]oxazin-2-one,
3-(4-Aminosulfanyloxyphenyl)-7-hydroxy-3,4-dihydro-benzo[e][1,3]oxazin-2-one,
3-(4-(tert.butyl)(dimethyl)silyloxyphenyl)-7-hydroxy-3,4-dihydro-benzo[e][1,3]oxazin-2-one,
3-(6.7.9.10.12.13.15.16.18.19-decahydro-5,8,11,14,17,20-hexaoxybenzocyclooctadecen-2yl)-7-hydroxy-3,4-dihydro-benzo[e][1,3]oxazin-2-one,
3-(Phenylmethyl)-7-hydroxy-3,4-dihydro-benzo[e][1,3]oxazin-2-one,
3-(4-Trifluoromethyloxyphenyl)-7-hydroxy-3,4-dihydro-benzo[e][1,3]oxazin-2-one,
3-(4-Methoxyphenyl)-3,4-dihydro-benzo[e][1,3]oxazin-2-one,
3-(Biphenyl-4-yl)-3,4-dihydro-benzo[e][1,3]oxazin-2-one,
3-(Naphth-1-yl)-7-hydroxy-3,4-dihydro-benzo[e][1,3]oxazin-2-one,
3-(4-Bromophenyl))-3,4-dihydro-benzo[e][1,3]oxazin-2-one,
3-(3-Aminosulfanyloxyphenyl)-7-aminosulfanyloxy-3,4-dihydro-benzo[e][1,3]oxazin-2-one,
3-Cyclohexyl-7-aminosulfanyloxy-3,4-dihydro-benzo[e][1,3]oxazin-2-one,
3-(4-Aminosulfanyloxyphenyl)-7-aminosulfanyloxy-3,4-dihydro-benzo[e][1,3]oxazin-2-one,
3-(4-Methoxyphenyl)-7-aminosulfanyloxy-3,4-dihydro-benzo[e][1,3]oxazin-2-one,
3-Phenyl-7-aminosulfanyloxy-3,4-dihydro-benzo[e][1,3]oxazin-2-one,
3-(4-Hydroxyphenyl)-7-aminosulfanyloxy-3,4-dihydro-benzo[e][1,3]oxazin-2-one, and
3-(Phenylmethyl)-7-aminosulfanyloxy-3,4-dihydro-benzo[e][1,3]oxazin-2-one.

In another aspect the resent invention provides a compound of formula

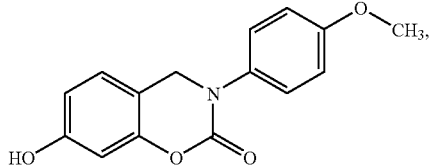

Compounds provided by the present invention are herein designated also as "compound(s) of (according to) the present invention".

A compound of the present invention includes a compound in any form, e.g. in free form, in the form of a salt, in the form of a solvate and in the form of a salt and a solvate.

In another aspect the present invention provides a compound of the present invention in the form of a salt.

A salt of a compound of the present invention includes a pharmaceutically acceptable salt, e.g. including a metal salt or an acid addition salt. Metal salts include for example alkali or earth alkali salts, acid addition salts include salts with organic acids and with inorganic acids, e.g. with HCl. A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of the present invention may exist in the form of isomers and mixtures thereof; e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racamtes. Substituents at any asymmetric carbon atom may be present in the (R)—, (S)— or (R;S)-configuration, preferably in the (R)— or (S)— configuration.

For example, a substituent bound to a cycloalkyl, e.g. wherein a substituent is bound in other position than para in a cyclohexyl, in the meaning of $R_1$ in a compound of formula I may be in the (R)— or (S)-configuration with respect to the 7-hydroxy-3,4-dihydro-benzo[e][1,3]oxazin-2-one group also bound to said cycloalkyl.

Isomeric mixtures may be separated as appropriate, e.g. according to a method as conventional, to obtain pure isomers. The present invention includes a compound of the present invention in any isomeric form and in any isomeric mixture. The present invention also includes tautomers of a compound of formula I, where tautomers can exist.

In another aspect the present invention provides a process for the production of a compound of formula I a. reacting a compound of formula

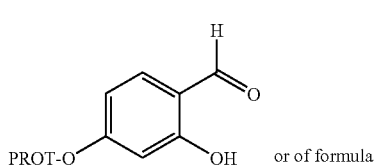

II or of formula

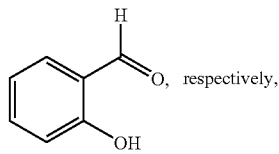

IIA respectively, wherein PROT is a hydroxy protecting group, e.g. benzyl, with a compound of formula $H_2N — R_1$ wherein $R_1$ is as defined above in the presence of a reducing agent, such as $NaBH_4$, to obtain a compound of formula

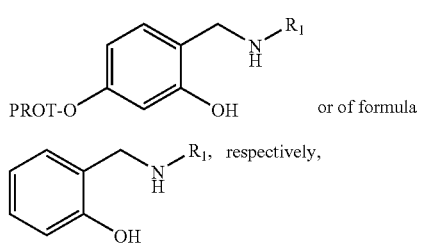

III or of formula

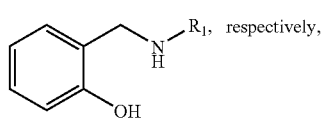

IIIA respectively, b. reacting a compound of formula III or of formula IIIA, respectively, obtained with carbonyldiimidazole in the presence of a base, e.g. triethylamine, to obtain a compound of formula

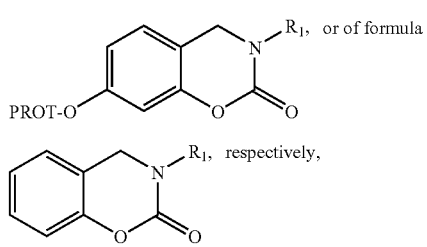

IV or of formula

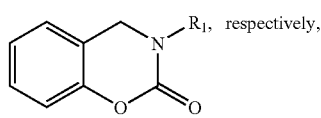

IVA respectively, c. optionally, if $R_1$ comprises a substituent which is hydroxy, reacting said hydroxy group to obtain a substituted hydroxy group with a reactive derivative of said substituent, e.g. in case that $R_1$ in a compound of formula I comprises a substituent which is tri($C_{1-6}$)alkylsilyloxy, reacting with a tri($C_{1-6}$)alkylsilylhalogenide, such as a chloride, e.g. in the presence of imidazole, e.g. in case that $R_1$ in a compound of formula I is aminosulfonyloxy, reacting a hydroxy group with amidochlorosulfonic acid, d. optionally deprotecting, i.e. removal of the protecting group PROT, e.g. by catalytic hydrogenation, to obtain a compound of formula I, e. optionally, if a compound of formula II is used as a starting material, reacting the hydroxy group obtained in step d. to obtain a substituted hydroxy group with a reactive derivative of said substituent, e.g. in case that $R_2$ in a compound of formula I is tri($C_{1-6}$)alkylsilyloxy reacting the hydroxy group obtained in step d. with a tri($C_{1-6}$)alkylsilylhalogenide, such as a chloride, e.g. in the presence of imidazole, e.g. in case that $R_2$ is aminosulfonyloxy reacting the hydroxy group obtained in step d. with amidochlorosulfonic acid, and e. isolating a compound of formula I obtained.

Any compound described herein, e.g. a compound of the present invention, may be prepared as appropriate, e.g. according, e.g. analogously, to a method as conventional, e.g. or as specified herein. A compound of formula II or of formula III is known or may be obtained according, e.g. analogously, to a method as conventional.

We have identified surprisingly the compounds of the present invention as MIF inhibitors by their inhibition of the enzymatic activity of MIF in vitro. The natural substrates of MIF enzyme activity are not yet known with certainty. However, the tautomerase activity of MIF can be readily demonstrated with the substrates D-dopachrome and p-hydroxyphenylpyruvate (HPP) (Rosengren et al. Molec. Med. 2:143-149, 1996; Rosengren E, FEBS Lett. 417:85-88, 1997). The assay used herein is such HPP assay adapted to the microtiter plate format:

Human MIF protein is purified according to Bernhagen et al. Biochemistry, 33:14144-14155, 1994. Dilutions of the enzyme are prepared in 50 mM sodium phosphate buffer, 1 mM EDTA, pH 6.5.

HPP is obtained from Aldrich. A stock solution of 60 mM HPP in ethanol is prepared and kept for maximally 4 hours on ice. The working solution (600 μM) of the substrate is prepared by diluting an aliquot of the stock solution with 50 mM sodium phosphate buffer, 1 mM EDTA, pH 6.5.

UV-transparent microtiter plates (96-well) are obtained from Corning (Cat#3635). Inhibitor and enzyme solutions are pipetted manually using an Eppendorf 12-channel pipette. Addition of substrate to start the reaction is performed with an Igel 96 pipetting station (OpalJena, Jena, Germany), which allows simultaneous addition of fluid to all 96 wells of the plates.

Optical density (OD) is determined using a SPECTRAmax 250 reader (Molecular Devices). The reader is operated with the SoftmaxPro 2.6.1 software.

Assay: Three wells of the microtiter plates are filled with buffer only, to allow for blanking. Into the test wells are pipetted consecutively:

50 μl inhibitor dilution (or buffer for control),

50 μl enzyme dilution (55 nM; final concentration in assay: 18.3 nM),

50 μl freshly diluted substrate working solution (600 μM; final concentration: 200 μM).

The last step is performed using the 96-channel pipetting device. The plate is then immediately (i.e. within a few seconds) transferred manually to the SPECTRAmax 250 reader and the optical density is determined (310 nm).

From the data obtained, $IC_{50}$ values are calculated using Excel™ and XLfit™ software.

The compounds of the present invention show activity in that assay, i.e. they inhibit MIF-(tautomerase)-enzymatic activity and are therefore indicated for use as pharmaceuticals, e.g. for the treatment of diseases mediated by MIF. Typically, the compounds show inhibition of MIF tautomerase activity with half-maximal inhibition ($IC_{50}$) within a range of 20 nM to 20 μM. A preferred compound is the compound of Example 2, which shows $IC_{50}$=20 nM, The compounds of the present invention are indicated for the treatment or prevention of diseases mediated by MIF.

Diseases mediated by MIF, e.g. inflammatory diseases, autoimmune diseases, neuropathic disorders and cancer, e.g. including transplantation, e.g. include diseases associated with cytokine-mediated toxicity, e.g. including interleukin-2 toxicity, diseases associated with the bone, e.g. including osteoporosis, diseases associated with the brain and the nerves, e.g. including conditions associated with the hypothalamic-pituitary-adrenal axis, neurodegenerative diseases, cerebrovascular diseases, central nervous infections, traumatic diseases, Alzheimer's disease, brain disorders, including trauma and inflammatory consequences of trauma, diseases associated with the eye, e.g. including uveoritinitis, vitreoretinopathy, corneal disease, iritis, iridocyclitis, cateracts, uveitis, diabetic retinopathy, diseases associated with the gastrointestinal tract e.g. including colitis, inflammatory bowel disease, colitis, Crohn's disease, ulcerative colitis, peptic ulceration, gastritis, oseophagitis, diseases associated with the heart and vascular conditions e.g. including heart diseases, proliferative vascular disease, vasculitides, polyarteritis nodosa, inflammatory consequences of ischaemia, ischaemic heart disease, myocardial infarction, stroke, peripheral vascular disease, pulmonary hypertension, diseases associated with the liver and the kidneys, e.g. including cirrhosis, hepatitis, sclerosing cholangitis, primary billiary cirrhosis, diseases associated with the respiratory tract and lung e.g. including pulmonary diseases, chronic pulmonary disease, acute (adult) respiratory distress syndrome (ARDS), asthma, asthma bronchitis, bronchiectasis, diffuse interstitial lung diseases, pneumoconioses, fibrosing aveolitis, diseases associated with skin and connective tissue diseases e.g. including eczema, atopic dermatitis, contact dermatitis, psoriasis, dermatomyositis, Sjörgen's syndrome, Churg-Strauss syndrome, sunburn, skin cancer, wound healing, diseases associated with allergic diseases, e.g. including delayed-type hypersensitivity, allergic rhinitis, diseases associated with angiogenesis, e.g. including diseases characterised by modified angiogenesis, tumor associated angiogenesis, diseases associated with cell overproliferation, e.g. including premalignant conditions, hyperproliferative disorders, cancers whether primary or metastatic, cervical and metastatic cancer, solid tumors, tumor growth, lymphoma, B-cell or T-cell lymphoma, premalignant conditions, benign tumors, benign dysproliferative disorders, renal carcinoma, esophageal cancer, stomach cancer, renal carcinoma, bladder cancer, breast cancer, colon cancer, lung cancer, melanoma, nasopharyngeal cancer, osteocarcinoma, ovarian cancer, uterine cancer; prostate cancer, skin cancer, leukemia, tumor neovascularization, angiomas, myelodysplastic diseases, diseases associated with diabetic diseases, e.g. including diabetes, diabetic retinopathy, insulin-dependent diabetes, diabetes mellitus, diseases associated with endiometriosis, testicular dysfunctions, diseases associated with infectious diseases, e.g. with chronic infectious diseases,
  e.g. including bacterial diseases, otitis media, Lyme disease, thryoditis, viral diseases, parasitic diseases, fungal diseases, malaria, e.g. malaria anemia, sepsis, severe sepsis, septic shock, e.g. endotoxin-induced septic shock, exotoxin-induced toxic shock, infective (true septic) shock, septic shock caused by Gram-negative bacteria, pelvic inflammatory disease, AIDS,
diseases associated with myasthenia gravis,
diseases associated with nephritis,
  e.g. including glomerulonephritis, interstitial nephritis, Wegener's granulomatosis,
diseases associated with pain,
diseases associated with rheumatic diseases,
  e.g. including arthritis, rheumatoid arthritis, osteoarthritis, psoriatic arthritis, crystal arthropathies, gout, pseudogout, calcium pyrophosphate deposition disease, lupus syndromes, systemic lupus erythematosus, sclerosis, sclerodema, multiple sclerosis, artherosclerosis, arteriosclerosis, spondyloarthropathies, systemic sclerosis, reactive arthritis, Reiter's syndrome, ankylosing spondylitis, polymyositis,
diseases associated with sarcoidosis,
diseases associated with transplantation,
  e.g. including graft versus host disease, failure accompanying rejection in organ transplantation, transplant rejection, protecting transplant organs;
  such as treatment or prevention of inflammatory diseases, autoimmune diseases, neuropathic disorders and cancers, e.g. including diseases following transplantation.

Preferred is the treatment or prevention of diseases associated with the gastrointestinal tract, including colitis, inflammatory bowel disease, Crohn's disease, colitis ulcerative colitis; and diseases associated with rheumatic diseases,.such as arthritis, rheumatoid arthritis.

In another aspect the present invention provides a compound of the present invention for use as a pharmaceutical, e.g. for diseases mediated by MIF, such as treatment or prevention of inflammatory diseases, autoimmune diseases, neuropathic disorders and cancers, e.g. including diseases following transplantation;
  e.g. including diseases associated with cytokine-mediated toxicity, the bone, the brain, the nerves, the eye, the gastrointestinal tract, the heart and vascular diseases, the liver and the kidneys, the respiratory tract and lung, skin and connective tissue diseases, allergic diseases, angiogenesis, cell overproliferation and cancers, diabetic diseases, endiometriosis, testicular dysfunctions, infectious diseases, myasthenia gravis, nephritis, pain, rheumatic diseases, sarcoidosis, and for the treatment and prevention of diseases following transplantation.

In a further aspect the present invention provides the use of a compound of the present invention for the manufacture of a medicament, e.g. a pharmaceutical composition, for the treatment or prevention of diseases mediated by MIF, e.g. such as described above.

In another aspect the present invention provides a method for the treatment or prevention of diseases mediated by MIF, e.g. such as described above, comprising. administering a therapeutically effective amount of a compound of the present invention to a subject in need of such treatment.

Treatment includes treatment and prophylaxis (prevention).

For such treatment, the appropriate dosage will, of course, vary depending upon, for example, the chemical nature and the pharmacokinetic data of a compound of the present invention employed, the individual host, the mode of administration and the nature and severity of the disease being treated.

A "pharmaceutically effective amount" as used herein is meant to be such amount of a compound of the present invention that results in a reduction in the development or severity of a disease characterized by MIF release and production. Toxicity and therapeutic efficacy of such compounds can be determined by standard pharmaceutical, pharmacological, and toxicological procedures in cell cultures or experimental animals, e.g., for determining the $LD_{50}$ (the dose lethal to 50% of the population) and the $ED_{50}$ (the dose therapeutically effective in 50% of the population), e.g. data obtained from cell culture assays or animal studies may be used for dose determination for the use in humans. The dosage of a compound of the present invention is preferably within a range of circulating concentrations that include the $ED_{50}$ (or the $ED_{99}$) with little or no toxicity. Dosaging may be dependent upon the dosage form applied and the route of administration. The exact pharmaceutical composition, route of administration and dosage may be chosen by the individual physician in view of the patient's condition. (see e.g. Fingl et al., 1975, in "The Pharmacological Basis of Therapeutics", Ch. 1 p. 1).

Dosage amount and interval may be adjusted individually to provide plasma levels of the active moiety which are sufficient to maintain the desired activity, or minimal inhibitory concentration (MIC). The MIC will vary for each compound but can be estimated from in vitro data; e.g., the concentration necessary to achieve a 50-97% inhibition of MIF-activity. Dosages necessary to achieve the MIC will depend on individual characteristics and route of administration. However, HPLC assays, bioassays or immunoassays can be used to determine plasma concentrations. Dosage intervals may also be determined using the MIC value. Compounds should be administered using a regimen that maintains plasma levels above the MIC for 10-90% of the time, preferably between 30-90% and most preferably between 50-90%.

However, in general, for satisfactory results in larger mammals, for example humans, an indicated daily dosage is in the range of from about 0.5 mg to 1000 mg (e.g. from about 0.00625 mg/kg to about 12.5 mg/kg) of an active compound of the present invention conveniently administered, for example, in divided doses up to four times a day.

A compound of the present invention may be administered by any conventional route, for example enterally, e.g. including nasal, buccal, rectal, oral, administration; per-enterally, e.g. including intravenous, intramuscular, subcutaneous administration; or topically, e.g. including epicutaneous, intranasal, intratracheal administration; e.g. in form of coated or uncoated tablets, capsules, injectable solutions or suspensions, e.g. in the form of ampoules, vials, in the form of creams, gels, pastes, inhaler powder foams, tinctures, lip sticks, drops, sprays, or in the form of suppositories.

The compounds of the present invention may be administered in the form of a pharmaceutically acceptable salt, e.g. an acid addition salt or metal salt, or in free form; optionally in the form of a solvate. The compounds of the present invention in the form of a salt exhibit the same order of activity as the active compounds of the present invention in free form; optionally in the form of a solvate.

In another aspect the present invention provides a pharmaceutical composition comprising a compound of the present invention, e.g. at least one, in association with at least one pharmaceutical excipient, e.g. appropriate carrier and/or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

The pharmaceutical compositions of the present invention may be manufactured analogously to a method as conventional, e.g., by mixing, dissolving, dragee-making, levitating, emulsifying, encapsulating, entrapping, or lyophilizing processes, e.g. using one or more pharmaceutically acceptable excipient, e.g. comprising carriers, diluents and auxiliaries that facilitate processing of the compounds of the present invention into pharmaceutical compositions. Useful techniques for formulating and administration of the compounds of the present invention may be found e.g. in "Remington's Pharmaceutical Sciences" Mack Publishing Co., Easton, Pa., latest addition.

Pharmaceutical compositions e.g. include pharmaceutical compositions for
- oral administration, such as tablets, pills, dragees, capsules, liquids, gels, syrups, slurries, suspensions for oral ingestion;
- buccal administration, e.g. in the form of tablets or lozenges,
- administration by inhalation, e.g. wherein a compound of the present invention is conveniently delivered in the form of an aerosol spray from pressurized packs or a nebulizer, e.g. with the use of a suitable propellant, or in the form of capsules and cartridges of e.g., gelatin for use in an inhaler or insufflator may be formulated containing a powder mix of the compound and a suitable powder base such as lactose or starch.
- parenteral administration by injection, e.g., by bolus injection or continuous infusion, e.g. in unit dosage form, such as ampoules or in multi-dose containers, wherein a pharmaceutical composition of the present invention is e.g. in the form of suspensions, solutions or emulsions, e.g. in oily or aqueous vehicles, optionally comprising further formulating agents such as suspending, stabilizing and/or dispersing agents; alternatively, the active ingredient may be in powder form for constitution with a suitable vehicle (liquid), e.g. water, before use.
- rectal administration, such as suppositories or retention enemas, e.g., containing conventional suppository bases such as cocoa butter or other glycerides.
- topical administration, e.g. including gels, creams.

One compound, or more than one compounds, of the present invention may be used for pharmaceutical treatment according to the present invention alone, or in combination with one or more other pharmaceutically active agents.

Other pharmaceutically agents include such as useful for the treatment of diseases mediated by MIF, e.g. including such which are useful for the treatment of inflammatory diseases, autoimmune diseases, neuropathic disorders and cancers, e.g. including diseases following transplantation. Such other pharmaceutically active agents include e.g. steroids, glucocorticoids, inhibitors of other inflammatory cytokines (e.g. anti-TNF-alpha antibodies, anti-IL-1 antibodies, anti-IFN-γ antibodies), or other cytokines such as IL-1RA or IL-10, other agents that decreases the endogenous amount of intracellular or extracellular MIF, such as MIF-antibodies, other MIF-LMW inhibitors, HMG-CoA reductase inhibitors, fibrate-type antihyperlipidemic drugs, anticancer agents, or immunomodulatory compounds, e.g. including immunosuppressants; or combinations of individual agents, e.g. as cited above.

Such immunomodulatory compounds include immunosuppressants, including e.g. corticosteroids; azathioprene; calcineurin inhibitors, such as cyclosporines, e.g. including cyclosporine A; mTOR-inhibitors, such as rapamycins, e.g. including rapamycin, 32-deoxorapamycin, 16-pent-2-ynyloxy-32-deoxorapamycin, 16-pent-2-ynyloxy-32 (S)-dihydro-rapamycin, 16-pent-2-ynyloxy-32(S)-dihydro-40-0-(2-hydroxyethyl)-rapamycin, 40-0-(2-hydroxyethyl)-rapamycin(everolimus), CC1779, AP23573, AP22549, inhibitors of the enzyme inosine 5'-monophosphate dehydrogenase (IMPDH), such as mycophenolic acid, including mycophenolic acid in the form of a salt, e.g. mycophenolate mofetil; macrophilin-12 binding compounds, such as ascomycins, e.g. including FK506 (tacrolimus), S1P receptor modulators, such as FTY720 and immunosuppressant antibodies, e.g. including immunosuppressive monoclonal antibodies, e.g. monoclonal antibodies to CD3, CD4, CD25, CD28, or CD45; or other immunomodulatory compounds.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising as an active ingredient a compound of the present invention, e.g. at least one, in combination, e.g. including fixed combinations, kits and free combinations, with one or more other pharmaceutically active agents, e.g. which other pharmaceutically active agents, e.g. selected from the group consisting of steroids, glucocorticoids, inhibitors of other inflammatory cytokines (e.g., anti-TNF-alpha antibodies, anti-IL-1 antibodies, anti-IFN-γ antibodies), other cytokines such as IL-1RA or IL-10, other agents that decreases the endogenous amount of intracellular or extracellular MIF, such as MIF-antibodies, other MIF-LMW inhibitors, HMG-CoA reductase inhibitors, fibrate-type antihyperlipidemic drugs, anticancer agents, or immunomodulatory compounds; or combinations of individual agents, e.g. as cited above, in association with, e.g. at least one, pharmaceutically acceptable excipient.

In another aspect the present invention provides 7-hydroxy-3,4-dihydro-benzo[e][1,3]oxazin-2-ones which are substituted at the nitrogen atom by unsubstituted or substituted $(C_{3-8})$cycloalkyl, $(C_{1-4})$alkyl$(C_{3-8})$cycloalkyl, $(C_{6-18})$aryl, or $(C_{6-18})$aryl$(C_{1-4})$alkyl, e.g. including a compound of formula

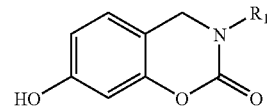

I wherein $R_1$ is unsubstituted or substituted $(C_{3-8})$cycloalkyl, $(C_{1-4})$alkyl$(C_{3-8})$cycloalkyl, $(C_{6-18})$aryl, $(C_{6-18})$aryl$(C_{1-4})$alkyl, wherein $(C_{6-18})$aryl is optionally annelated with another ring (system) and wherein substituents are selected from the group consisting of unsubstituted and substituted hydroxy;

e.g. $R_1$ is cyclohexyl, hydroxycyclohexyl, phenyl, hydroxyphenyl, methoxyphenyl, aminosulfonyloxyphenyl, (tert-butyl)(dimethyl)silyloxyphenyl, phenylmethyl, or phenyl anellated with a 18-crown-6, such as benzo-18-crown-6.

In the following examples which illustrate the invention references to temperature are in degrees Centigrade (° C.) and are uncorrected.

The following abbreviations are used:
EX.: Example EtOH: ethanol
m.p.: Melting point RT: room temperature

EXAMPLE 1

Production of 3-Cyclohexyl-7-hydroxy-3,4-dihydro-benzo[e][1,3]oxazin-2-one of formula

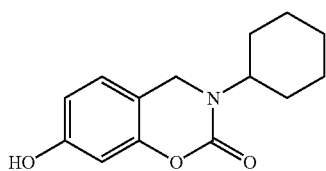

A. 3-Cyclohexyl-7-methoxy-3,4-dihydro-benzo[e][1,3]oxazin-2-one 40 g of cyclohexylamine are added to a solution of 26 g of 2-hydroxy-4-methoxy-benzaldehyde in 800 ml of absolute EtOH at RT. The mixture obtained is stirred for 1.5 hours, cooled to 0°, and 20 g of $NaBH_4$ are added in portions. The mixture obtained is stirred for 3 hours at RT, poured into $H_2O$ and the mixture obtained is extracted with $CH_2Cl_2$. Two phases are formed and are separated. The organic layer obtained is dried, 42 g of carbonyl-diimidazole are added and the mixture obtained is stirred for 16 hours at RT. Additional 21.5 g of carbonyl-diimidazole are added, the mixture obtained is stirred for 3 hours, washed with 1N HCl, a saturated, aqueous solution of $NaHCO_3$ and brine, dried and concentrated in vacuo. 3-Cyclohexyl-7-methoxy-3,4-dihydrobenzo[e][1,3]-oxazin-2-one is obtained. m.p.: 76-77°.

$^1$H-NMR (CDCl$_3$): δ6.99 (d, J=8.4 Hz, 1 H), 6.66 (dd, J=2.5+8.4 Hz, 1 H), 6.57 (d, J=2.5 Hz, 1 H), 4.30 (s, 2 H), 4.24 (tt, J=3.6+11.6 Hz, 1 H); 3.78 (s, 3 H), 1.33-1.90 (m, 9 H), 1.02-1.20 (m, 1 H).

A sample of the compound obtained according to step A. is subjected to flash chromatography on silica gel and the fractions comprising purified 3-cyclohexyl-7-methoxy-3,4-dihydro-benzo[e][1,3]oxazin-2-one are treated with HCl. 3-cyclohexyl-7-methoxy-3,4-dihydro-benzo[e][1,3]oxazin-2-one in the form of a hydrochloride is obtained. m.p.: 169-172°.

$^1$H-NMR (CDCl$_3$) δ6.86 (d, J=8.25 Hz, 1 H), 6.41 (d, J=2.55 Hz, 1 H), 6.33 (dd, J=2.55+8.25 Hz, 1 H), 3.96 (s, 2 H), 3.76 (s, 3 H), 2.53 (tt, J=3.7+10 Hz, 1 H) 1.92-2.03 (m, 2 H), 1.56-1.80 (m, 3 H), 1.03-1.37 (m, 5 H).

B. Production of 3-Cyclohexyl-7-hydroxy-3,4-dihydro-benzo[e][1,3]oxazin-2-one A mixture of 66 g of 3-cyclohexyl-7-methoxy-3,4-dihydro-benzo[e][1,3]oxazin-2-one and 200 g of pyridinium HCl are heated without solvent on a metal bath to 220° for 45 minutes whilst stirring. Evolving HCl gas is sucked off. The mixture obtained is cooled to RT, the melt obtained is dissolved in $H_2O$ and ethyl acetate and two phases obtained are separated. The aqueous layer obtained is extracted with ethyl acetate and washed with 1N HCl, dried and concentrated in vacuo. The residue obtained is filtered over silica gel and the filtration residue obtained is concentrated. 3-Cyclohexyl-7-hydroxy-3,4-dihydro-benzo[e][1,3]oxazin-2-one is obtained in crystalline form. m.p. 193-196°.

$^1$H-NMR (CDCl$_3$) δ7.19 (br.s, 1 H), 6.95 (d, J=8.3 Hz, 1 H), 6.65 (dd, J=2.4+8.3 Hz, 1 H), 4.30 (s, 2 H), 4.23 (tt, J=3.6+11.6 Hz, 1 H), 1.30-1.90 (m, 9 H), 1.02-1.20 (m, 1 H).

EXAMPLE 2

Production Process for the Compound of EX. 17 in TABLE 1 Below

Production of 3-cyclohexyl-7-aminosulfonyloxy-3,4-dihydro-benzo[e][1,3]oxazin-2-one 22.5 g of 3-cyclohexyl-7-hydroxy-3,4-dihydro-benzo[e][1,3]oxazin-2-one are treated with 42.3 g of amidochlorsulfonic acid without solvent. The mixture obtained is stirred at 60° under reduced pressure (100 mbar) for 1 hour. The mixture obtained is cooled to RT, ethyl acetate and water are added and the the mixture is extracted. The organic layer obtained is dried and concentrated in vacuo. 3-Cyclohexyl-7-aminosulfonyloxy-3,4-dihydro-benzo[e][1,3]oxazin-2-one is obtained.

$^1$H-NMR (DMSO-d$_6$): d 8.06 (br.s, 2 H), 7.36 (d, J=8.3 Hz, 1 H), 7.06 (dd, J=2.3+8.3 Hz, 1 H), 6.96 (d, J=2.3 Hz, 1 H), 4.46 (s, 2 H), 3.99 (tt, J=3.6+11.6 Hz, 1 H), 1.20-1.84 (m, 9 H), 1.00-1.19 (m, 1 H). 13C NMR (d6-DMSO): d 25.376, 25.641, 29.039, 41.450, 56.165, 109.794, 117.801, 118.292, 127.513, 149.593, 150.048, 150.211.

Analogously as set out in Example 1 and optionally Example 2, but using appropriate starting materials, compounds of formula

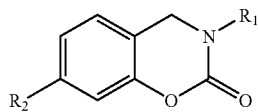

are obtained wherein $R_1$ and $R_2$ are as set out in TABLE 1 having the melting point ("F.p.") and/or "$^1$H-NMR-data" ($^1$H-NMR-data are determined in CDCl$_3$, if not otherwise indicated).

TABLE 1

| EX. | $R_1$ | $R_2$ | F.p./$^1$H-NMR/MS |
|---|---|---|---|
| 1 | cyclohexyl | OH | 193-196° |

TABLE 1-continued
| EX. | R₁ | R₂ | F.p./¹H-NMR/MS |
|---|---|---|---|
| 2 | 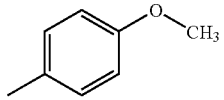 | OH | 212-215° |
| 3 | 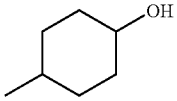 | OH | 239-247° |
| 4 | 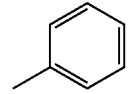 | OH | 4.78 (s, 2H), 5.96-6.65 (m, 2H), 6.88-7.06 (m, 1H), 7.22-7.50 (m, 5H), 8.98 (bs, 1H) |
| 5 | 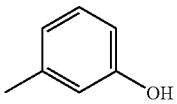 | OH | 226-228° |
| 6 | 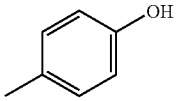 | OH | 6.44 (d, 1H), 6.56 (dd, 1H), 6.74-6.82 (m, 2H), 7.03 (d, 1H), 7.20-7.26 (m, 2H), 9.58 (bs, 1H), 9.78 (bs, 1H) |
| 7 | 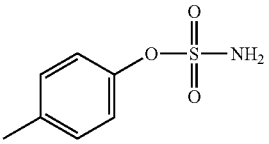 | OH | 224-227° |
| 8 | 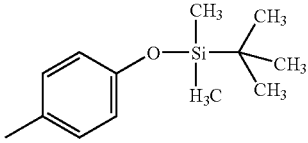 | OH | 212-216° |
| 9 | 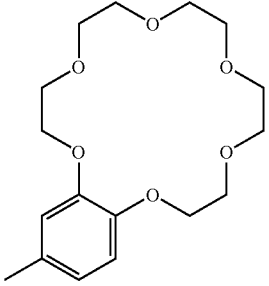 | OH | 167-169° |
| 10 | 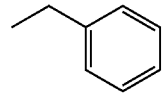 | OH | 164-169° |
| 11 | 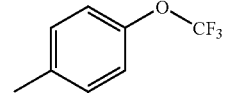 | OH | 204-208° |
| 12 | 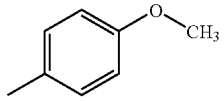 | H | 141-143° |

TABLE 1-continued

| EX. | R₁ | R₂ | F.p./¹H-NMR/MS |
|---|---|---|---|
| 13 | 4-phenylphenyl-CH₂– (biphenyl-4-ylmethyl) | H | 217-219° |
| 14 | naphthalen-1-ylmethyl | OH | 242-244° |
| 15 | 4-bromobenzyl | H | 163-164° |
| 16 | 3-(sulfamoyloxy)benzyl | NH₂—SO₂—O— | 90-99° |
| 17 | cyclohexylmethyl | NH₂—SO₂—O— | 179-184° |
| 18 | 4-(sulfamoyloxy)benzyl | NH₂—SO₂—O— | 53-55° |
| 19 | 4-methoxybenzyl | NH₂—SO₂—O— | 196-199 |
| 20 | benzyl | NH₂—SO₂—O— | 197-199 |
| 21 | 4-hydroxybenzyl | NH₂—SO₂—O— | 186-189° |
| 22 | 2-phenylethyl | NH₂—SO₂—O— | 176-179° |

The invention claimed is:
1. 3-(substituted phenyl)-3,4-dihydro-benzo[e][1,3]oxazin-2-ones,
3-((C₁₀₋₁₈)aryl)-3,4-dihydro-benzo[e][1,3]oxazin-2ones,
3-((C₃₋₈)cycloalkyl)-3,4-dihydro-benzo[e][1,3]oxazin-2-ones,
3-((C₈₋₁₂)aryl(C₁₋₄alkyl)-3,4-dihydro-benzo[e][1,3]oxazin-2-ones, and

3-($C_{3-8}$)cycloalkyl($C_{1-4}$alkyl)-3,4-dihydro-benzo[e][1,3]oxazin-2-ones.

2. A compound according to claim 1 of formula

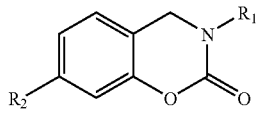

I wherein
$R_1$ is substituted phenyl, or
$R_1$ is unsubstituted or substituted
  ($C_{3-8}$)cycloalkyl($C_{1-4}$)alkyl,
  ($C_{6-18}$)aryl($C_{1-4}$alkyl,
  ($C_{3-8}$)cycloalkyl,
  ($C_{10-18}$)aryl,
wherein substituents are selected from the group consisting of ($C_{6-18}$)aryl, halogen, hydroxy, aminosulfonyloxy, ($C_{1-4}$)alkoxy, tri($C_{1-4}$)alkylsilyloxy, halo($C_{1-4}$)alkyl and halo($C_{1-4}$) alkoxy,
$R_2$ is hydrogen, hydroxy, aminosulfonyloxy, ($C_{1-4}$)alkoxy, tri($C_{3-6}$)alkylsilyloxy, or halo($C_{1-4}$)alkoxy.

3. A compound according to claim 2, wherein
$R_1$ is
  cyclohexyl,
  hydroxycyclohexyl,
  biphenylyl,
  napththyl,
  hydroxyphenyl,
  methoxyphenyl,
  trifloromethoxyphenyl,
  bromophenyl,
  aminosulfonyloxyphenyl,
  (tert-butyl)(dimethyl)silyloxyphenyl, or
  phenyl annelated with a 18-crown-6, and
R is as defined in claim 2.

4. A compound according to claim 2, wherein
$R_2$ is
  hydrogen,
  hydroxy, or
  aminosulfonyloxy.

5. A compound according to claim 1 of formula

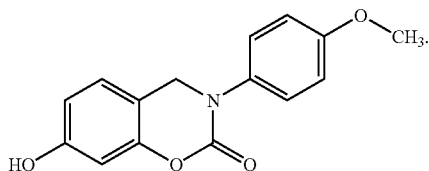

6. A compound of claim 1 in the form of a salt.

7. A pharmaceutical composition comprising a compound of claim 1 in association with at least one pharmaceutical excipient.

8. A compound according to the formula

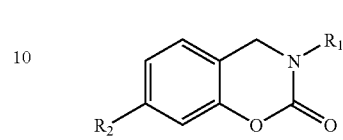

I wherein
$R_1$ is unsubstituted or substituted
  ($C_{3-8}$)cycloalkyl($C_{1-4}$)alkyl,
  ($C_{6-18}$)aryl($C_{1-4}$)alkyl,
  ($C_{3-8}$)cycloalkyl,
  ($C_{6-18}$)aryl,
  wherein substituents are selected from the group consisting of ($C_{6-18}$)aryl, halogen, hydroxy aminosulfonyloxy, ($C_{1-4}$)alkoxy, tri($C_{1-6}$)alkylsilyloxy, halo($C_{1-4}$)alkyl and ($C_{1-4}$)alkoxy,
$R_2$ is hydroxy, aminosulfonyloxy, ($C_{1-4}$)alkoxy, tri($C_{1-6}$)alkylsilyloxy or halo($C_{1-4}$)alkoxy.

9. A compound according to claim 8, wherein
$R_1$ is
  cyclohexyl,
  hydroxycyclohexyl,
  phenyl,
  biphenylyl,
  napththyl,
  hydroxyphenyl,
  methoxyphenyl,
  trifloromethoxyphenyl,
  bromophenyl,
  aminosulfonyloxyphenyl,
  (tert-butyl)(dimethyl)silyloxyphenyl, or
  phenyl annelated with a 18-crown-6, and
$R_2$ is as defined in claim 8.

10. A compound according to claim 8, wherein
$R_2$ is
  hydroxy,
  aminosulfonyloxy.

* * * * *

UNITED STATES PATENT AND TRADEMARK OFFICE
CERTIFICATE OF CORRECTION

PATENT NO.        : 7,378,416 B2  
APPLICATION NO. : 11/576610  
DATED              : May 27, 2008  
INVENTOR(S)      : Billich et al.

It is certified that error appears in the above-identified patent and that said Letters Patent is hereby corrected as shown below:

Col. 17 line 67, Claim 1, should be changed from "3-(($C_{8-12}$)aryl" to "3-(($C_{6-12}$)aryl"

Col. 19 line 38, Claim 3, should be changed from "R is as defined in claim 2" to "$R_2$ is as defined in claim 2"

Signed and Sealed this

Twentieth Day of October, 2009

David J. Kappos  
*Director of the United States Patent and Trademark Office*